(12) United States Patent
Emi

(10) Patent No.: US 6,245,502 B1
(45) Date of Patent: *Jun. 12, 2001

(54) TARGET SYSTEM

(76) Inventor: Bernhard Emi, Kaenelgasse 17, Zollikofen (CH), 3052

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/026,904

(22) Filed: Feb. 19, 1998

(30) Foreign Application Priority Data

Feb. 19, 1997 (EP) .................................................. 97102616

(51) Int. Cl.$^7$ ................................. C12Q 3/00; C12N 9/12
(52) U.S. Cl. ................................................ 435/4; 435/194
(58) Field of Search ......................................... 435/4, 194

(56) References Cited

U.S. PATENT DOCUMENTS 5,698,428 * 12/1997 Abo ........................................ 435/194
5,700,675 * 12/1997 Rubin .................................... 435/194

OTHER PUBLICATIONS

Ammer et al., 1979, "Phosphorylation of streptozotocin during uptake via the phosphoenolpyruvate: sugar phosphotransferase system in *Escherichia coli*", Antimicrob. Agents Chemother. 16:801–807.

Amster–Choder and Wright, 1993, "Transcriptional regulation of the bgl operon of *Escherichia–coli* involves phosphotransferase system–mediated phosphorylation of a transcriptional antiterminator", J. Cell. Bioch. 51:83–90.

Buhr et al., 1992 "The glucose transporter of *Escherichia coli*. Mutants with impaired translocation activity that retain phosphorylation activity", J. Biol. Chem. 267:3847–3851.

Christian et al., 1992, "Simplified methods for construction, assessment and rapid screening of peptide libraries in bacteriophages ", J. Mol. Biol. 227:711–718.

Curtiss III and Kelly, 1987, "*Salmonella typhimurium* deletion mutants lacking adenylate cyclase and cyclic AMP receptor protein are avirulent and immunogenic", Infect. Immun. 55:30355–3043.

Curtiss III et al., 1988, "Avirulent *Salmonella typhimurium* Δcya Δcrp oral vaccine strains expressing a streptococcal colonization and virulence antigen", Vaccine 6:155–160.

Eberstadt et al., 1966, "Solution structure of the IIB domain of the glucose transporter of *Escherichia coli*", Biochemistry 35:11286–11292.

(List continued on next page.)

Primary Examiner—Michael Borin

(57) ABSTRACT

The bacterial phosphotransferase system (PTS) as a drug target system catalyses the uptake and phosphorylation of carbohydrates. It is further involved in signal transduction, e.g. catabolite repression, chemotaxis, and allosteric regulation of metabolic enzymes and transporters. It is ubiquitous in bacteria but does not occur in eukaryotes. This uniqueness and the pleiotropic function make the PTS a target for the development of new antimicrobials. Assays are described that lead to the discovery of compounds which uncouple the PTS, by acting as protein histidine/cysteine phosphatases. Uncoupling of the PTS leads to inhibition of carbohydrate transport, repression of catabolite controlled genes (e.g. certain virulence genes) and depletion of phosphoenolpyruvate. Compounds from combinatorial libraries with high affinity for phosphoenolpyruvate-protein-phosphatase (Enzyme 1) serve as lead structures for the development of inhibitors and uncouplers of the PTS.

8 Claims, 4 Drawing Sheets

OTHER PUBLICATIONS

Figure 1:
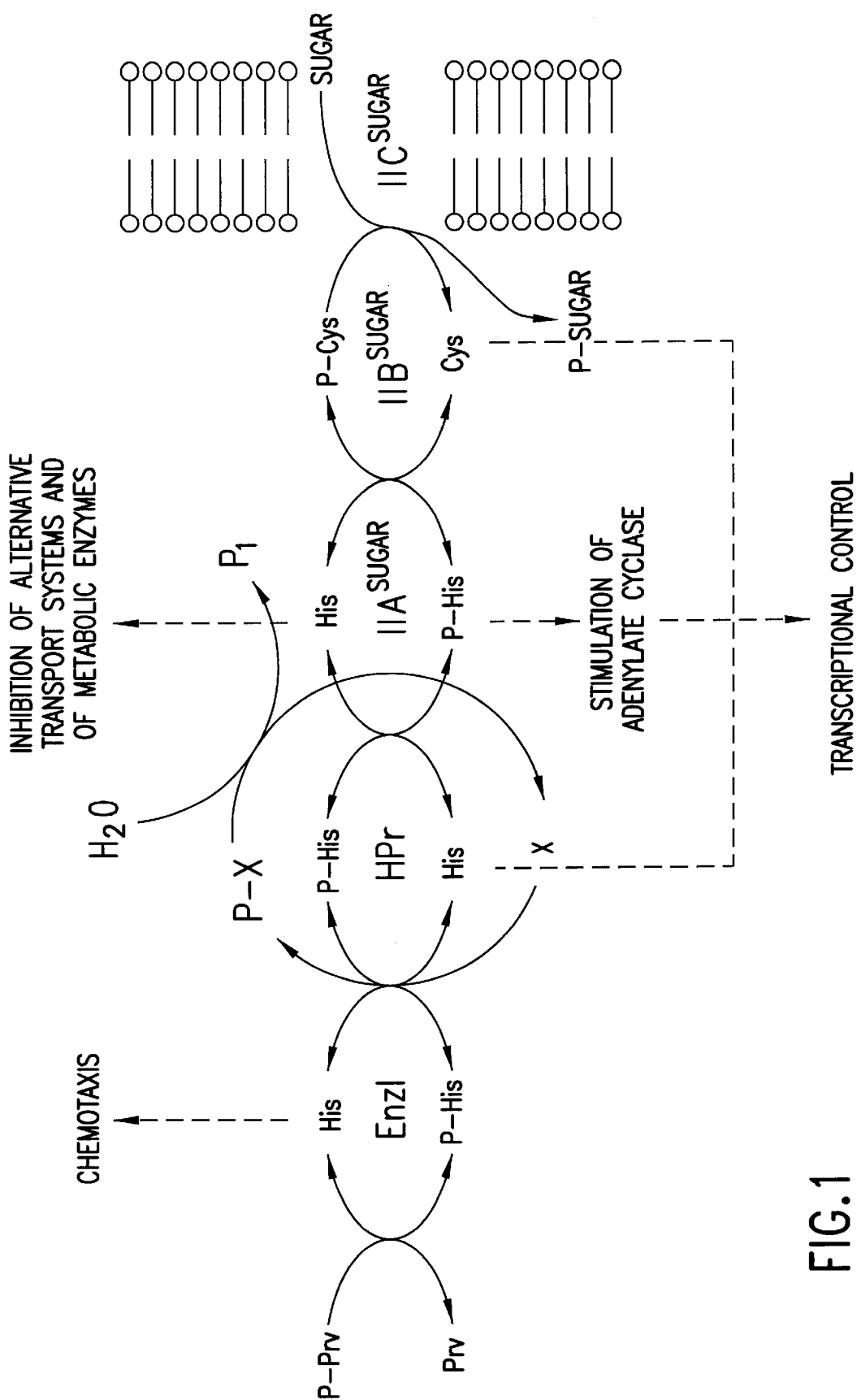

Erni et al., 1982, "Bacterial phosphotransferase system. Solubilization and purification of the glucose–specific enzyme II from membranes of *Salmonella typhimurium*", J. Biol. Chem. 257:13726–13730.

Erni, 1992, "Group translocation of glucose and other carbohydrates by the bacterial phosphotransferase system", Int. Rev. Cytol. 137A:127–148.

Hurley et al., 1993, "Structure of the regulatory complex of *Eschierichia coli*III$^{Glc}$ with glycerol kinase", Science 259:673–677.

Jia et al., 1993, "Active–centre torsion–angle strain revealed in 1.6 angstrom–resolution structure of histidine–containing phosphocarrier protein", Nature 361:94–97.

Jia et al., 1993, "The 2.0–angstrom resolution structure of *Escherichia coli* histidine–containing phosphocarrier protein HPr –A redetermination", J. Biol. Chem. 268:22490–22501.

Kalbitzer and Hengstenberg, 1993, "The solution structure of the histidine–containing protein (Hpr) from *Staphylococcus–aureus* as determined by 2–dimensional H–1–NMR spectroscopy", Eur. J. Biochem. 216:205–214.

Kelly et al., 1992, "Characterization and protective properties of attenuated mutants of *Salmonella choleraesuis*"Infect. Immun. 60:4881–4890.

Lengeler et al., 1994, "Enzymes II of the phosphoenolpyruvate–dependent phosphotransferase systems: their structure and function in carbohydrate transport", Biochem. Biophys. Acta 1188:1–28.

Liao et al., 1996, "The first step in sugar transport: crystal structure of the amino terminal domain of enzyme I of the *E. coli* PEP: sugar phosphotransferase system and a model of the phosphotransfer complex with HPr", Structure 4:861–872.

Lux et al., 1995, "Coupling the phosphotransferase system and the methyl–accepting chemotaxis protein–dependent chemotaxis signaling pathways of *Escherichia coli*", Proc. Natl. Acad. Sci. USA 92:11583–11587.

Licalsi et al., 1991, "Sugar transport by the bacterial phosphotransferase system. Structural and thermodynamic domains of Enzyme I of Salmonella typhimurium", J. Biol. Chem. 266:19519–19527.

Mao et al., 1995, "Functional reconstitution of the purified mannose phosphotransferase system of *Escherichia coli*. into phospholipid vesicles", J. Biol. Chem. 270:5258–5265.

Martin,–Verstraete et al., 1994 "Interactions of wild–type and truncated LevR of *Bacillus subtilis* with the upstream activating sequence of the levanase operon", J. Biol. 241:178–192.

Mayahara et al., 1967, "The new lead citrate method for the ultrachemical demonstration of activity of non–specific alkaline phosphatase", Histochemie 11:88.

Meadow et al.,1990, "The bacterial phosphoenolpyruvate:glycose phosphotransferase system", Annu. Rev. Biochem. 59:497–542.

Meins et al., 1993, Cysteine phosphorylation of the glucose transporter of *Escherichia coli*. J. Biol. Chem. 268, 11604–11609.

Mukhija and Erni, 1996, "Purification by Ni$^{2+}$ affinity chromatography, and functional reconstitution of the transporter for N–acetylglucosamine of *Escherichia coli*", J. Biol. Chem. 271:14819–14824.

Nishikawa et al., 1995, "Catabolite repression of the adhesion of Vero cytotoxin–producing Escherichia coli serogroups 01557 an 0111", Microb. Pathog. 18:223–229.

Postma et al., 1993, "Phosphoenolpyruvate: carbohydrate phosphotransferase systems in bacteria", Microbiol. Rev. 57:543–594.

Powell et al., 1995, "Novel proteins of the phosphotransferase system encoded within the *rpoN* operon of *Eschericia coli*", J. Biol. Chem. 270:4822–4839.

Rajagopal et al., 1994, "Structural consequences of histidine phosphorylation: NMR characterization of the phosphohistidine form of histidine–containing protein from *Bacillus subtilis* and *Escherichia coli*", Biochemistry 33:15271–15282.

Reizer et al., 1993, "Sequence analyses and evolutionary relationships among the energy–coupling proteins enzyme–I and HPr of the bacterial phosphoenolpyruvate–sugar phosphotransferase system", Protein Sci. 2:506–521.

Roossien et al., 1983, "A simple procedure for the synthesis of [$^{32}$P ]phosphophoenolpyruvate via the pyruvate kinase exchange reaction at equilibrium", Biochim. Biophsy. Acta. 760:185–187.

Saier, 1993, "Regulatory interactions involving the proteins of the phosphotransferase system in enteric bacteria", J. Cell. Biochem. 51:62–68.

Saier and Reizer, 1994, "The bacterial phosphotransferase system: New frontiers 30 years later", Molecular Microbiology 13:755–764.

Saier et al., 1995, "Protein phosphorylation and regulation of carbon metabolism in Gram–negative versus Gram–positive bacteria", TIBS 20:267–271.

Scott and Smith, 1990, "Searching for peptide ligands with an epitope library", Science 249:386–390.

Seok et al., 1996, "Importance of the carboxyl–terminal domain of enzyme I of the *Escherichia coli*phosphoenolpyruvate: sugar phosphotransferase system for phosphoryl donor specifity", Proc. Natl Acad Sci. USA 93:347–351.

van Nuland et al., 1992, "Determination of the 3–dimensional solution structure of the histidine–containing phosphocarrier protein HPr from *Escherichia coli* using multi-dimensional NNR spectroscopy", Eur. J. Bioch. 210:881–891.

van Nuland et al., 1995, "High–resolution structure of the phosphorylated form of the histidine–containing phosphocarrier protein HPr from *Escherichia coli*determined by restrained molecular dynamics from NMR–NOE data", J. Mol. Biol. 246:180–193.

Weber et al., 1995, "Optimierung der biologischen Aktivitä t von kombinatorischen Verbindungsbibliotheken durch einen genetischen Algorithmus", Angew. Chem. 107:2452–2454.

Wittekind et al., 1992, "Solution structure of the phosphocarrier protein HPr from *Bacillus subtilis* by two–dimensional NMR spectroscopy", Protein Sci. 1:1363–1376.

LiCalsi et al., J. Biol. Chem., 266:19519–19527, Oct. 1991.*

Seok et al. Proceedings Natl Acad. Sci. USA, 93:347–351, Jan. 1996.*

Postma et al. Microbiol. Rev., 57, 543–594, Sep. 1993.*

Powell et al. J. Biol. Chem. 270:4822–4839, Mar. 1995.*

* cited by examiner

TARGET SYSTEM

This application claims benefit of European Patent Application No. 97102616.6, filed Feb. 19, 1997, incorporated herein by reference it its entirety.

1. INTRODUCTION

The invention relates to a drug target system for the identification of novel and highly specific antimicrobials. In particular, the present invention relates to screening assays to identify antimicrobial agents which uncouple or inhibit the bacterial phosphotransferase system.

2. BACKGROUND OF THE INVENTION

Infectious diseases affect all age groups and cause one-third of all death worldwide. Respiratory infections, diarrheal diseases and tuberculosis, neonatal tetanus and whooping cough are the most prominent among the bacterial infections. Infectious disease are still rising due to population growth, urbanization, and not least due to the widespread use of antibiotics that led to the development of antibiotic resistance. The increasing incidence of bacterial drug-resistance requires that new targets of antimicrobial therapy be identified and that inhibitors of these systems be discovered.

3. SUMMARY OF THE INVENTION

The present invention relates to a drug target system for novel and specific antimicrobials which modulate the bacterial phosphotransferase system. In particular, the present invention relates to the identification of agents which uncouple or inhibit the bacterial phosphotransferase system. In a preferred embodiment of the present invention, the assays to identify antimicrobial agents which a) use a phosphoryl group acceptor which is not part of the phosphotransferase system and preferably hydrolyse spontaneously or under the influence of non- specific endogenous phosphohydrolases thereby uncoupling the phosphotransferase system, or b) inhibit the phosphotransferase system activity by blocking or inactivating at least one of the enzymes of the phosphotransferase system.

The present invention relates to screening assays to identify potential antimicrobial agents which screen for those agents which utilize a phosphoryl group that is not part of the bacterial phosphotransferase system, or agents which hydrolyse, spontaneously or under the influence of non-specific endogenous phosphohydrolases, thereby uncoupling the system. The present invention further relates to screening assays to identify agents which inhibit at least one of the enzymes of the phosphotransferase system.

Furthermore, the invention relates to novel antimicrobials identified by using said drug target system.

4. BRIEF DESCRIPTION OF THE DRAWINGS

FIG. 1. The bacterial phosphoenolpyruvate dependent phosphotransferase system. Phosphoryl groups are sequentially transferred from phosphoenolpyruvate (P-Prv) to HPr and hence to the different transporters for carbohydrates and polyalcohols ($IIA^{sugar}$, $IIB^{sugar}$, $IIC^{sugar}$. Enzyme I, the $IIA^{Glc}$ subunit of the glucose transporter, the $IIB^{\beta gl}$ subunit of the β-glucoside transporter of *E. coli* and of possibly other gram negative bacteria, and HPr of *B. subtilis* and other gram positive bacteria have regulatory functions. X is the hypothetical inhibitor. Ideally, X should be phosphorylated by enzyme I and then hydrolyse spontaneously, thereby uncoupling the protein phosphorylation.

Figure 2:
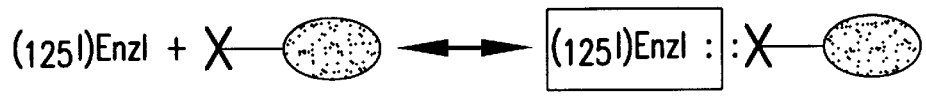
Figure 2:
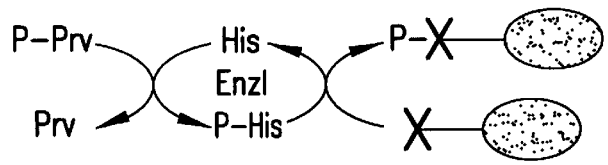
Figure 2:
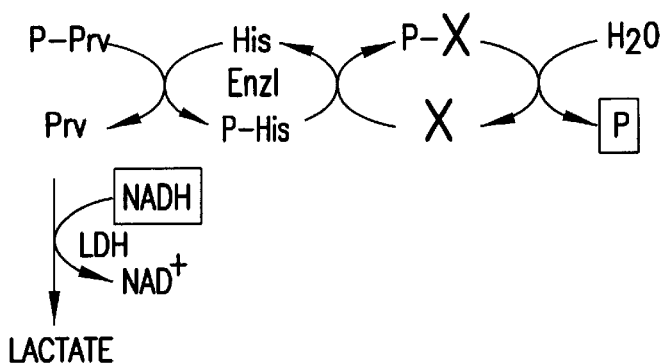
Figure 2:
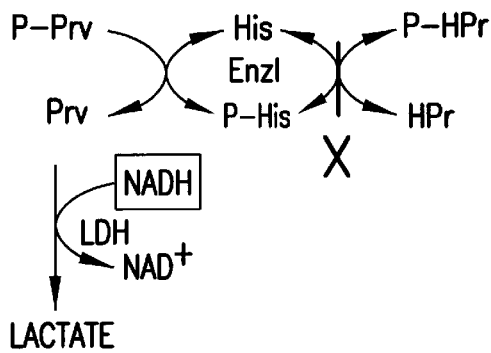
Figure 2:
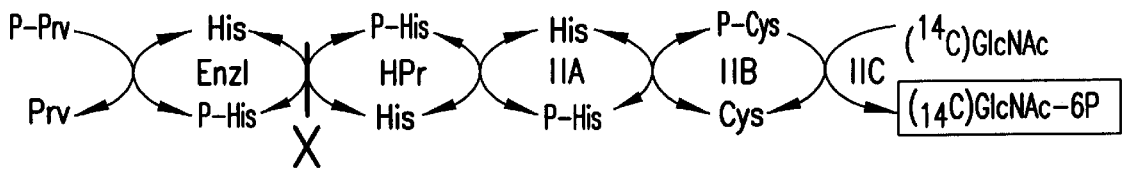

FIG. 2. Assays for the screening, selection and characterization of inhibitory compounds from combinatorial libraries. Reaction products that can be determined experimentally are boxed. The inhibitory compound X can be in soluble form, immobilized on a filamentous phase, or bound to a microtiter well. The transporter for GlcNAc (shaded in grey) contains the IIA, IIB and IIC functional units as domains of a single polypeptide chain.

Figure 3:
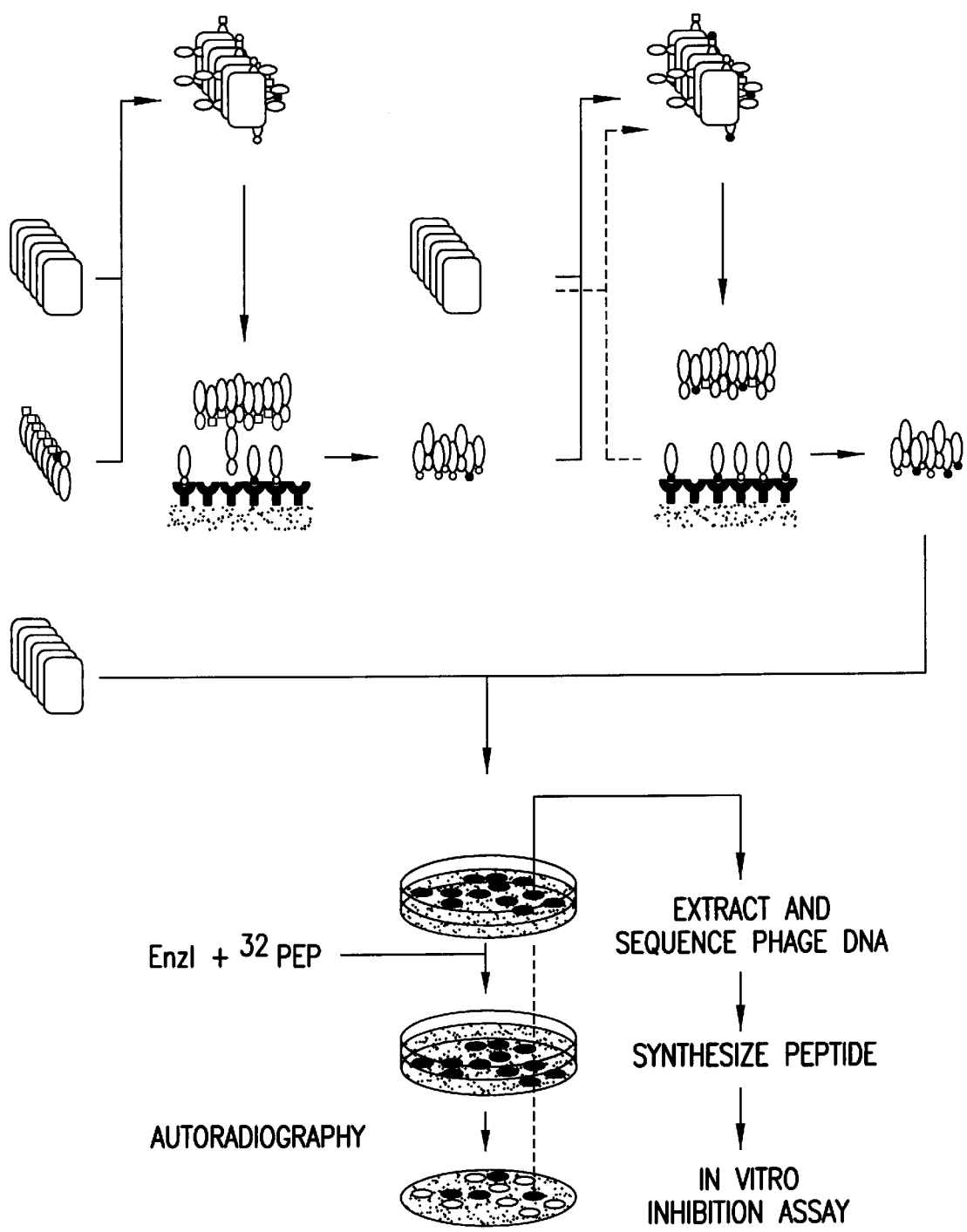

FIG. 3. Selection of Enzyme I-binding peptides from phage display libraries. M13 phages were panned with enzyme I (top of figure) to enrich for enzyme I binding phages. *E. coli* clones transfected with "high affinity" phages were then grown on nitrocellulose sheets, and the secreted and nitrocellulose bound phages were incubated over night with an overlay of enzyme I in the presence of [$^{32}$P] phosphoenolpyruvate. Phosphorylated phage were identified with the PhosphorImager and sequenced. The phage displayed sequences which became phosphorylated 25 to 30 fold over average were chemically synthesized and their biological activity was characterized. Results are summarized in Table I.

Figure 4A:
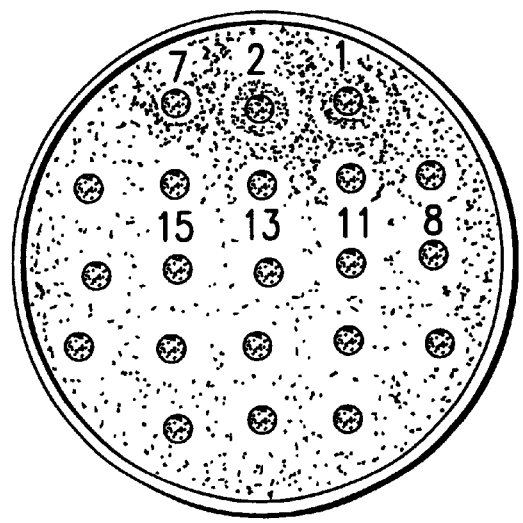
Figure 4B:
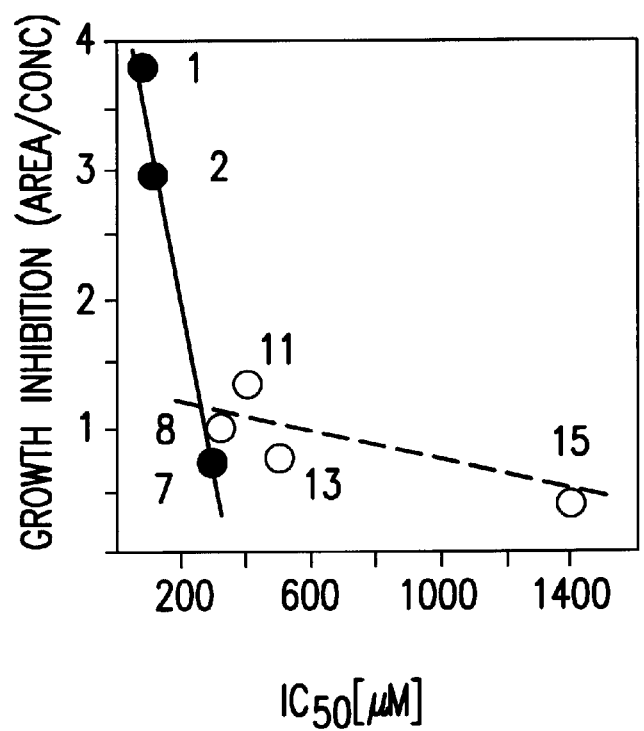

FIG. 4. Growth inhibition of *E. coli* K12 UT580. Peptides were added to filter discs and placed onto a cell culture in LB soft agar. The clear zones are indicative of growth inhibition (panel A). The growth inhibitory activity of the peptides is inversely correlated with their $IC_{50}$ (panel B). The number refer to the peptides listed in Table I.

5. DETAILED DESCRIPTION OF THE INVENTION

The present invention relates to novel antimicrobials which inhibit or uncouple the bacterial phosphotransferase system. In a particular embodiment, the present invention relates to agents which utilize a phosphoryl group acceptor which is not part of the phosphotransferase system and preferably hydrolyse spontaneously or under the influence of a non-specific endogenous phosphohydrolases, thereby uncoupling the phosphotransferase system. In another embodiment, the present invention relates to agents which inhibit the phosphotransferase system by blocking or inactivating at least one of the enzymes of the system.

The present invention further relates to screening assays to identify agents which utilize a phosphoryl group acceptor which is not part of the phosphotransferase system or agents which hydrolyse spontaneously or under the influence of a non-specific endogenous phosphohydrolase as a potential anti-microbial agent. The present invention further relates to screening assays to identify agents which inhibit or block any of the enzymes of the phosphotransferase system.

The present invention further relates to pharmaceutical compositions comprising the novel antimicrobial agents which target the bacterial phosphotransferase system. The present invention still further relates to methods of treating or preventing diseases or disorders caused by infection with a microbial agent.

5.1. The Phosphotransferase System

The present invention relates to agents which target the phosphotransferase system and therefore have utility as an antimicrobial agent. The present invention further relates to screening assays to identify those agents which target the phosphotransferase system, as potential antimicrobial agents. In accordance with the present invention, the enzymes, phosphoryl donors and acceptors, transporters and other components of the phosphotransferase system which may serve as targets are described in detail below.

The PTS plays a dual role in transport and phosphorylation of carbohydrates and hexitols on one hand and in signal transduction on the other. The molecular basis of its dual function is a protein phosphorylation cascade comprising four phosphoprotein units which sequentially transfer phosphoryl groups from phosphoenolpyruvate to the transported carbohydrates or polyalcohols (FIG. 1). Phosphoryltransfer occurs through phosphohistidine and phosphocysteine intermediates (for review see Meadow et al., 1990, Annu. Rev. Biochem. 59: 497–549; Erni, 1992, Int. Rev. Cytol. 137A: 127–148; Postma et al., 1993, Microbiol. Rev. 57: 543–594; Saier and Reizer, 1994, Molecular Microbiology 13: 755–764; Saier et al., 1995 TIBS 20: 267–271). The first unit in the cascade phosphoenolpyruvat-protein-phosphatase termed enzyme I (Enz 1) (EC 2.7.3.9.), is a soluble two-domain protein (LiCalsi et al., 1991 J. Biol. Chem. 266: 19519–19527; Seok et al., 1996 Proc. Natl. Acad Sci. USA 93:347–351). It catalyses the phosphoryltransfer from phosphoenolpyruvate to the second component, the small (9 kD) soluble phosphorylcarrier protein HPr. HPr itself then serves as phosphoryldonor to the different PTS transporters (sugar and/or polyalcohol specific IIA, IIB, IIC subunits, called phosphotransferase enzyme II A, phosphotransferase enzyme II BC, all numbered EC 2.7.1.69; Lengeler et al., 1994 Biochem. Biophys. Acta 1188:1–28). The transporters mediate sugar and polyalcohol uptake by a mechanism that couples translocation with phosphorylation of the transported solute. (FIG. 1).

In addition to the transport and the phosphorylation of sugars and/or polyalcohols the PTS also regulates a variety of physiological processes in both gram-negative and gram-positive bacteria, e.g. catabolite repression, transport of carbohydrates which are not substrates of the PTS, carbon and energy metabolism, carbon storage, the coordination of nitrogen with carbon metabolism, and chemotaxis (Powell, et al., 1995 J. Biol. Chem. 270:4822–4839; Saier and Reizer, 1994 Molecular Microbiology 13:755–764). Signal transduction by the PTS is based on the cyclic interconversion of the proteins between phosphorylated and non-phosphorylated forms. The two forms regulate allosterically and by phosphorylation the activity of metabolic enzymes and transcription factors (for review see Postma et al., 1993 Microbiol. Rev. 57: 543–594). The concentration of the dephosphorylated form of PTS proteins increases when PTS sugars are present and taken up by the cell. The phosphorylated species predominate in the absence of PTS substrates. Phosphorylated IIA of gram-negative bacteria stimulates adenylate cyclase and thereby the cAMP dependent transcription of the catabolite controlled genes (FIG. 1). Dephosphorylated IIA inhibits glycerolkinase (Hurley et al., 1993 Science 259: 673-677), the transporters for maltose, lactose, melibiose, raffinose, and most likely other as yet unknown enzymes (for reviews see Saier, 1993; Titgemeyer et al., 1994 J. Bacteriol. 176:543–546; Saier et al., 1995 TIBS 20:267–271).

In gram-positive bacteria HPr instead of IIA is involved in catabolite repression (Saier et al., 1995). HPr of gram-positive bacteria is phosphorylated at Ser46 by an ATP dependent Hpr specific protein kinase. Phosphorylated HPr acts as corepressor by binding to the Catabolite control protein A (CcpA) repressor thereby increasing the affinity of CcpA for the regulatory DNA region (reviewed in Saier et al., 1995 TIBS 20:267–271).

Recent studies have uncovered that catabolite repression plays a role in the expression of virulence factors. S. typhimurium lacking adenylate cyclase are avirulent for mice (Curtiss and Kelly, 1987 Infect. Immunol. 55:30355–30403; Curtiss et al., 1988 Vaccine 6:155–160). Similarly a S. choleraesuis mutant lacking a functional adenylate cyclase was avirulent indicating that genes involved in cell attachment or invasion may be under catabolite control (Kelly et al., 1992 Infect. Immunol. 60: 4881–4890). Vero cytotoxin-producing E. coli showed marked inhibition of adhesion when grown in the presence of the PTS sugar mannose, further suggesting that the expression of virulence genes might be controlled by the PTS via catabolite repression (Nishikawa et al., 1995 Microb. Pathology 18: 223–229).

However, it must be mentioned that the PTS functions are not necessary for growth of E. coli on a complex medium in the laboratory. But PTS Enz I mutants cannot grow on defined media containing PTS substrates as the only carbon source. They also do not grow or grow with difficulty on other defined media containing non-PTS substrates.

As stated above, the bacterial phosphotransferase system is a target of antimicrobial therapy, in particular, since the PTS is ubiquitous in bacteria but does not occur in eukaryotic cells. This minimizes the toxic side effects. The PTS, unlike cell wall synthesis or DNA replication, continues to be active and therefore vulnerable in nongrowing and slow-growing cells. Metabolic energy is required in stationary phase cells long after replication and cell division are arrested.

5.2. Antimicrobial Agents which Target the Phosphotransferase System

An antimicrobial agent targeting the PTS of the invention can have the following functional properties: (i) It can interrupt the flow of phosphoryl groups along the phosphorylation cascade with the effect that PTS proteins remain dephosphorylated. Dephosphorylated proteins erroneously signal that PTS sugars are abundant even if they are not present in the medium. As a consequence virulence factors under catabolite control cannot be expressed and alternative nutrients that might be present in the host cannot be metabolized efficiently. (ii) It can act as protein histidine phosphatase towards enzyme I or any other PTS protein. This way, the agent will not only block but also uncouple the phosphoryl transfer chain with the effect that phosphoenolpyruvate would be consumed in a futile cycle. This will deprive the cell of an energy carrier for substrate level phosphorylation and of an important building block for biosynthetic reactions (anaplerotic synthesis of oxalacetate, gluconeogenesis, aromatic amino acid biosynthesis). The two effects, depletion of phosphoenolpyruvate and repression of catabolite controlled genes are enough to compromise cell growth and infectivity.

Of all the PTS proteins, enzyme I is preferably—but not exclusively—the target of choice for the following reasons:

Enzyme I has been found in all bacteria containing a PTS system. There are at least seventeen enzyme I sequences listed in the ENBL protein data bank. A comparison of the complete genomes of e.g. *Mycoplasma genitalium, Haemophilus influenzae* and the almost complete genome of *E. coli* confirms, that enzyme I and HPr are always present. For comparison, the number and types of sugar specific PTS transporters strongly varies between different species.

Enzyme I of the PTS appears to be one of the best conserved proteins with maximal amino acid sequence similarity in the prokaryotic kingdom and minimal aminoacid sequence similarity to any protein from the eukaryotic kingdom. For this reason it can be expected, that an inhibitor/uncoupler of Enzyme I should have a strong selectivity for its target and, hence, a very reduced—if at all—side effect profile regarding eukaryotic cells.

Enzyme I transfers phosphorylgroups from phosphoenolpyruvate to the phosphorylcarrier protein HPr. This is the first reaction in the divergent cascade (compare FIG. 1). Therefore, its inhibition has the most pleiotropic effect.

Using the above explained drug target system, antibacterial compounds directed against the bacterial phosphotransferase system, preferentially, but not exclusively directed against Enzyme I have been identified. To achieve this all the relevant PTS proteins of E. coli shown in FIG. 1 have been purified and reconstituted in vitro. With the availability of these agents, the following embodiments of the present invention may be achieved.

- Development of in vitro assays for the rapid screening of chemical compound and peptide libraries for binding to PTS proteins, inhibition of PTS activity, and for protein phosphatase activity.
- Search for chemical compounds and peptides inhibiting the phosphoryltransfer between enzyme I and HPr (compare Table I on page 16, in which examples of such peptides are listed).
- Search for chemical compounds and peptides with protein phosphatase activity.
- Conversion of compounds and peptides (which act as strong competitive inhibitors of enzyme I) into suicide-inhibitors and uncouplers. In one embodiment, the construction of uncouplers involves the substitution of the nucleophilic imidazole ring of the active histidine with an N-alkylimidazole, a thiazoliumring and/or other heterocyclic compounds of similar reactivity. Such groups react with the enzyme I bound phosphorylgroup like imidazole. However, unlike imidazolium phosphate, the N-alkylimidazolium/thiazolium phosphates cannot be stabilized by deprotonation and are hydrolyzed immediately. The construction of suicide inhibitors involves suitably substituted α,β-unsaturated thiols and other nucleophilic groups, which upon phosphorylation become good leaving groups (e.g. phosphate thioesters). Such leaving groups accelerate vinylogous nucleophilic substitutions by protein nucleophiles at the β-carbon.
- Search for chemical compounds and peptides or peptide conjugates inhibiting the PTS in bacteria using a bacterial screening assay for the discovery of chemical compounds which specifically inhibit the PTS.

5.3. Preferred Emodiments

In a preferred embodiment of the present invention, the antimicrobial agents are peptides selected from the group consisting of:

| SEQ ID No.: 1 | GLRFGKTRVHYLVLG |
| SEQ ID No.: 2 | SGRKSTRVHHWLLVL |
| SEQ ID No.: 3 | KMSRHRKPGA |
| SEQ ID No.: 4 | SSLRGHRWVY |
| SEQ ID NO.: 5 | KISRHGKRGK |
| SEQ ID NO.: 6 | KISRHGRPTG |
| SEQ ID NO.: 7 | RIHFIPRRGR |
| SEQ ID NO.: 8 | RLHYLF[a] |
| SEQ ID NO.: 9 | DGARLHYLF[a] |
| SEQ ID NO.: 10 | AcDGARLHYLF[a] |
| SEQ ID NO.: 11 | RHWSIF |
| SEQ ID NO.: 12 | RHRTLF |
| SEQ ID NO.: 13 | RHYLLF |
| SEQ ID NO.: 14 | RHITSL |
| SEQ ID NO.: 15 | RHITLF |
| SEQ ID NO.: 16 | MSRHRN |
| SEQ ID NO.: 17 | PNGLHTRPA[b] |
| SEQ ID NO.: 18 | MRLLKTLCFGLCG |
| SEQ ID NO.: 19 | AcMRLLKTLCFVGLCG |
| SEQ ID NO.: 20 | KKFHLRK |
| SEQ ID NO.: 21 | KKFALRK[a] |
| SEQ ID NO.: 22 | KKFDLRK[b] |
| SEQ ID NO.: 23 | XXKKWHLRKRXX |
| SEQ ID NO.: 24 | KKWHLRKR[c] |
| SEQ ID NO.: 25 | KGWHKRKK |
| SEQ ID NO.: 26 | KKWHRRKK |
| SEQ ID NO.: 27 | KKWHKRKK |
| SEQ ID NO.: 28 | KKFHIRKR |
| SEQ ID NO.: 29 | PNGLHTRPA[d] |
| SEQ ID NO.: 30 | Bio-PNGLHTRPA[c] |
| SEQ ID NO.: 31 | WHKR |
| SEQ ID NO.: 32 | Ac-WHKR[f] |

5.4. Antibiotic Agents Identified by Methods of the Invention

In one embodiment, the invention features novel antibiotic agents discovered by the methods described herein. These antibiotic agents are specific inhibitors of the bacterial transferase system in a target organism, such as infectious pathogenic microorganism. It also includes novel pharmaceutical compositions which include antibiotic agents discovered as described herein formulated in pharmaceutically acceptable formulations.

In another embodiment, the invention features a method for treating a subject infected with an infectious agent by administering to that subject a therapeutically effective amount of an antibiotic agent which is a specific inhibitor of the bacterial transferase system in the infectious agent as determined by the assays of the invention. Such administration can be by any method known to those skilled in the art, for example, by topical application or by systemic administration.

In yet another embodiment, antibiotic agents of the present invention can be used to treat contaminated items, such as crops, wood, metal or plastic and the like, by methods such as, but not limited to, spraying or dusting of that agent onto the contaminated item, or impregnating that agent into the item.

By "therapeutically effective amount" is meant an amount that relieves (to some extent) one or more symptoms of the disease or condition in the patient. Additionally, by "therapeutically effective amount" is meant an amount that returns to normal, either partially or completely, physiological or biochemical parameters associated with or causative of a bacterial disease or condition.

5.4.1. Formulation

The antibiotic compounds identified by methods of the invention may be formulated into pharmaceutical preparations for administration to animals for treatment of a variety of infectious diseases. Compositions comprising a compound of the invention formulated in a compatible pharmaceutical carrier may be prepared, packaged, labelled for treatment of and used for the treatment of the indicated infectious diseases caused by microorganisms, such as those listed infra in Section 5.4.3.

If the antibiotic compound is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, polyethylene glycol or glycerine. Thus, the compounds and their physiologically acceptable solvates may be formulated for administration by inhalation or insufflation (either through the mouth or the nose) or oral, buccal, parenteral, topical, dermal, vaginal, rectal administration and drug delivery device, e.g., porous or viscous material, such as lipofoam.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The antibiotic compounds may also be formulated in rectal compositions such as suppositories or retention enemas, e.g., containing conventional suppository bases such as cocoa butter or other glycerides.

In addition to the formulations described previously, the antibiotic compounds may also be formulated as a depot preparation. Such long acting formulations may be administered by implantation (for example, subcutaneously or intramuscularly) or by intramuscular injection. Thus, for example, the antibiotic compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The antibiotic compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The pharmaceutical compositions of the present invention comprise an antibiotic compound as the active ingredient, or a pharmaceutically acceptable salt thereof, and may also contain a pharmaceutically acceptable carrier, and optionally, other therapeutic ingredients, for example antivirals. The term "pharmaceutically acceptable salts" refers to salts prepared from pharmaceutically acceptable non-toxic acids and bases, including inorganic and organic acids and bases.

The pharmaceutical compositions include compositions suitable for oral, rectal, mucosal routes, transdermal, parenteral (including subcutaneous, intramuscular, intrathecal and intravenous), although the most suitable route in any given case will depend on the nature and severity of the condition being treated.

In practical use, an antibiotic agent can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, microcrystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives and the like know to those skilled in the art. Examples of such parenteral compositions include, but are not limited to Dextrose 5%w/v, normal saline or other solutions.

5.4.2. Administration

For administration to subjects, antibiotic compounds discovered by using the assays of the invention are formulated in pharmaceutically acceptable compositions. The compositions can be used alone or in combination with one another, or in combination with other therapeutic or diagnostic agents. These compositions can be utilized in vivo, ordinarily in a mammal, preferably in a human, or in vitro. In employing them in vivo, the compositions can be administered to the mammal in a variety of ways, including parenterally, intravenously, subcutaneously, intramuscularly, colonically, rectally, vaginally, nasally, orally, transdermally, topically, ocularly, or intraperitoneally.

As will be readily apparent to one skilled in the art, the magnitude of a therapeutic dose of an antibiotic compound in the acute or chronic management of an infectious disease will vary with the severity of the condition to be treated, the particular composition employed, and the route of administration. The dose, and perhaps dose frequency, will also vary according to the species of the animal, the age, body weight, condition and response of the individual subject. The determination of effective dosage levels, that is the dosage levels necessary to achieve the desired result, will be within the ambit of one skilled in the art.

Desirable blood levels may be maintained by a continuous infusion of an antibiotic compound as ascertained by plasma levels. It should be noted that the attending physician would know how to and when to terminate, interrupt or adjust therapy to lower dosage due to toxicity. Conversely, the attending physician would also know how to and when to adjust treatment to higher levels if the clinical response is not adequate (precluding toxic side effects).

In selected cases, drug delivery vehicles may be employed for systemic or topical administration. They can be designated to serve as a slow release reservoir, or to deliver their contents directly to the target cell. Such vehicles have been shown to also increase the circulation half-life of drugs which would otherwise be rapidly cleared from the blood stream. Some examples of such specialized drug delivery vehicles which fall into this category are liposomes, hydrogels, cyclodextrins, and bioadhesive microspheres. These vehicles have been developed for chemotherapeutic agents.

Topical administration of agents is advantageous when localized concentration at the site of administration with minimal systemic adsorption is desired. This simplifies the delivery strategy of the agent to the disease site and reduces the extent of toxicological characterization. Furthermore, the amount of material to be administered is far less than that required for other administration routes.

Antibiotic agents may also be systemically administered. Systemic absorption refers to the accumulation of agents in the blood stream followed by distribution throughout the entire body. Administration routes which lead to systemic absorption include: oral, intravenous, subcutaneous, intraperitoneal, intranasal, intrathecal and ocular. Each of these administration routes exposes the agent to an accessible target.

5.4.3. Target Infectious Agents

The antimicrobial agents of the present invention may be used for the treatment of diseases or disorders resulting from bacterial infection, in particular, respiratory infections, diarrheal diseases and tuberculosis, neonatal tetanus and whooping cough.

The antibiotic compounds identified by the methods of the infection can be used to treat infectious diseases in animals, including humans, companion animals (e.g., dogs and cats), livestock animals (e.g., sheep, cattle, goats, pigs, and horses), laboratory animals (e.g., mice, rats, and rabbits), and captive or wild animals. These infectious diseases are caused by a variety of infectious agents, such as but not limited to, bacteria, fungi, protozoa, and helminth parasites.

Specifically, infectious diseases caused by bacteria including but not limited to, gram positive cocci, such as Staphylococci (e.g., *S. aureus*), Streptococci (e.g., *S. pneumoniae, S. pyrogens, S. faecalis, S. viridans*); gram positive bacilli, such as Bacillus (e.g., *B. anthracis*), Corynebacterium (e.g., *C. diphtheriae*), Listeria (e.g., *L. monocytogenes*); gram negative cocci, such as Neisseria (e.g., *N. gonorrhoeae, N. Meningitidis*); gram negative bacilli, such as Haemophilus (e.g. *H. influenzae*), Pasteurella (e.g., *P. multocida*), Proteus (e.g., *P. mirabilis*), Salmonella (e.g., *S. typhi murium*), Shigella species, Escherichia (e.g., *E. coli*), Klebsiella (e.g., *K. pneumoniae*), Serratia (e.g. *S. marcescens*), Yersinia (e.g., *Y. pestis*), Providencia species, Enterobacter species, Bacteroides (e.g., fragilis), Acinetobacter species, Campylobacter (e.g., *C. jejuni*), Pseudomonas (e.g., *P. aeruginosa*), Bordetella (e.g., *B. pertussis*), Brucella species, Fracisella (e.g., *F. tularensis*), Clostridia (e.g., *C. perfriugens*), Helicobacter (e.g., *H. pylori*), Vibrio (e.g., *V. cholerae*), Mycoplasma (e.g., *M. pneumoniae*), Legionella (e.g., *L. pneumophila*), Spirochetes (e.g. Treponema, Leptospira and Borrelia), Mycobacteria (e.g., *M. tuberculosis*), Nocardia (e.g., *N. asteroides*), Chlamydia (e.g., *C. trachomatis*), and Rickettsia species, can be treated by antibiotic drugs discovered by the methods of the invention.

More particularly, systemic and local mycotic infections caused by fungi, such as Aspergillus (e.g., *A. fumigatus*), Candida (e.g., *C. albicans*), Coccidioides species, Histoplasma species, Blastomyces species, and Microsporum species, can be treated by antibiotic drugs discovered by the methods of the invention.

More particularly, infections caused by protozoa, such as Entamoeba (e.g., *A. histolytica*), Giardia species, Balantidium species, Cryptosporidium species, Trichomonas (e.g., *T. vaginalis*), Trypanosoma (e.g., *T. brucei, T. cruzi*), Leishmania (e.g., *L. donovani*), Plasmodium (e.g., *P. falciparum, P. vivax*), Toxoplamsma (e.g., *T. gondii*), and Pneumocystis (e.g., *P. carinii*), can be treated by antibiotic drugs discovered by the methods of the invention.

More particularly, infections caused by helminth parasites, such as nematodes (roundworms and hookworms, e.g., *Ascaris lumbricoides, Trichinella spiralis*), cestodes (tapeworms, e.g., *Taenia saginata*), and the Trematoda (flukes, e.g., Schistosoma species) can be treated by antibiotic drugs discovered by the methods of the invention.

5.5. Screening Assays

The following exemplification illustrates the screening assays of the present invention for the identification of agents which inhibit the bacterial phosphotransferase system. In particular, the agents may be screemed from chemical compound libraries or peptide phage display libraries for binding to PTS proteins, inhibition of PTS activity, and for protein phosphatase activity.

Several assays were developed to identify chemical compounds which (a) bind to Enzyme I and (b) are phosphorylated by Enzyme I (FIG. 2). A further assay (c) to detect ligands with phosphatase activity towards Enzyme I has also been developed (for details see *Materials and Methods* below).

(a) Binding of Enzyme I

To immobilized ligands, e.g. filamentous phages from a phage display library or synthetic peptides from a combinatorial peptide library was detected using [$^{125}$I]-Enzyme I and autoradiography.

(b) Phosphorylation by Enzyme I.

To identify peptides and filamentous phages displaying a peptide which can be phosphorylated by Enzyme I, support based peptide libraries and immobilized peptide-displaying phages were incubated over night with enzyme I in the presence of [$^{32}$P]phosphoenolpyruvate, and the phosphorylated species were detected with a PhosphorImager. The enzyme I dependent phosphorylation was confirmed by thin layer chromatography, autoradiography and by electrospray mass spectroscopy of the phosphorylated soluble peptides.

c) Phosphatase activity.

A conventional and well established assay to calorimetrically detect the formation of inorganic phosphate has been adapted to the specific needs. The assay can be performed in microtiter plates and quantitated with a microplate photoreader. Another assay to monitor phosphatase activity of soluble compounds is based on the detection of pyruvate which is continuously produced from phosphoenolpyruvate whenever enzyme I is dephosphorylated. The enzyme I-specific phosphatase activity of soluble compounds can be detected from the pyruvate burst. The rate of pyruvate formation is monitored with lactate dehydrogenase and NADH. The assay can be performed in microtiter plates and quantitated with a microplate photoreader.

(d) Inhibition of In Vitro PTS Activity.

The inhibitory activity of soluble compounds can be measured quantitatively in the sugar phosphotransferase assay in the presence of the purified PTS proteins and with [$^{14}$C]GlcNAc ([$^{14}$C]N-acetyl-glucosamine) or [$^{14}$C]Glc ([$^{14}$Clc ([$^{14}$C]glucose) as terminal phosphate acceptor (Erni et al., 1982 J. Biol. Chem. 257:13726–13730).

(e) Inhibition of PTS activity in bacteria.

Compounds that specifically interfere With the PTS can also be detected in bacteria. Indicator *E. coli* (or any other bacteria) will be plated on two defined minimal salts media containing either glucose or a non-PTS substrate e.g. lactose as the only carbon source. Compounds from chemical libraries are applied to both cultures. Agents that inhibit growth on glucose only but do not affect growth on non-PTS substrates are candidate PTS inhibitors.

5.6. Specific Embodiments

The invention may be better understood by the following description of illustrative embodiments which are not intended to be limiting.

In a particular embodiment of the present invention, potential inhibitors of the bacterial phosphotransferase system may be identified from peptides from phage display libraries, as described below.

Peptides from Phage Display Libraries

M13 phage display libraries expressing 6-mer, 9-mer, 10-mer and 15-mer inserts (Scott and Smith, 1990; Christian et al., 1992) were panned with enzyme I to enrich for enzyme I binding phases. *E. coli* clones transfected with "high affinity" phages were grown on nitrocellulose sheets, and the secreted and nitrocellulose bound phages were incubated over night with enzyme I in the presence of ($^{32}$P) phosphoenolpyruvate. Phosphorylated phages were identified with the PhosphorImager (commercially available from e.g. Molecular Dynamics) and sequenced. The sequences of the peptides which were phosphorylated 25 to 30 fold over the average are shown in Table 1. FIG. 3 on the next page illustrates this procedure.

All the phage displayed peptides contain either a histidine or a cysteine residue and all the peptides contain one or several basic residues. This is indicative of electrostatic stabilisation of the enzyme I-ligand complex between the positively charged peptide and the active site pocket of Enz I which contains a high proportion of acidic residues (Seok et al., 1996 Proc. Natl. Acad. Sci. USA 93:347–351). It is of particular interest that cysteine containing sequences appeared in addition to the expected His containing peptides. Indeed, certain PTS proteins (IIB domains of the PTS transporters, FIG. 1) are phosphorylated at cysteine (Meins et al. 1991 J. Biol. Chem. 268:11604–11609. It appears that the active site of enzyme I recognizes not only Ms but also Cys in an appropriate sequence context.

Inhibition of the PTS by Peptides

Some of the peptides from the phage display library which became phosphorylated by Enzyme I have been synthesized by standard methods in soluble form and characterized. They inhibit the in vitro phosphotransferase activity with IC$_{50}$ of between 60 μM and over 10 mM (Table I). The second part of FIG. 3 on the previous page illustrates this procedure.

Materials and Methods

Binding of enzyme I to immobilized peptides, monitored with [$^{125}$I]-enzyme I. Enzyme I was radiolabeled with $^{125}$I by the lactoperoxidase-catalyzed reaction following the procedure reported for gonadotropins. Briefly, 1 mg of Enzyme I in 200 μl of buffer was iodinated with 10 μl (0.5 mCi) of Na$^{125}$I. The reaction was conducted at 34° C. for 60 min in a water bath with gentle shaking throughout. The reaction was terminated by the addition of potassium iodide. Iodinated protein was separated from free iodine on a Sephadex G-50 column presaturated with BSA and equilibrated with 50 mM PBS (pH 7.2).

Cellulose membranes with immobilized peptides were incubated with 50 mM TBS containing 3% BSA for 1 hr with shaking at room temperature. Membranes were subsequently washed and further incubated for 1 hr with 50 mM PBS containing 0.15% casein, another blocking agent to block the non-specific binding sites. These membranes were then incubated with [$^{125}$I]-enzyme I in PBS containing 0.15% casein for 2 hr. Nonspecifically and weakly bound [$^{125}$I]-enzyme I was removed from the membranes by washing them with PBS containing 0.1 % Tween. Radioactivity was determined by autoradiography.

Enzyme I dependent phosphorylation of immobilized peptides. [$^{32}$P]-PEP was prepared as described by Roossien et al., 1983. Cellulose membranes with immobilized peptide libraries were treated with the blocking agents as described above. These libraries were then incubated for 30 min at room temperature with [$^{32}$P]-PEP in the presence of catalytic amounts of enzyme I. The phosphorylated species were identified with a PhosphoImager (Molecular Dynamics).

Inhibition of Phosphotransferase Activity by Soluble Peptides.

This assay measures the inhibition of enzyme I dependent sugar phosphorylation activity. The IC$_{50}$ is defined as the concentration of the inhibitor required for 50% inhibition of the PTS activity. The purified N-acetylglucosamine transporter (II$^{GlcNac}$) of E. coli (Mukhija and Erni, 1996) was used as the sugar specific component. The reaction mixture contained per 100 μl, 100 μg phosphatidyl glycerol from egg yolk (Sigma), 50 mM KPi, pH 7.5, 2.5 mM dithiothreitol, 2.5 mM NaF, 5 MM MgCl$_2$, 1 mM phosphoenolpyruvate (potassium salt, Sigma), 0.5 mM [U-$^{14}$C]GlcNAc (New England Nuclear; 56.3 mCi/mmol, diluted to 1000 cpm/nmol), and 3 μM each of purified HPr and enzyme I (Mao et al., 1995 J. Biol. Chem. 270:5258–5265). The reaction was started by addition of 0.1 μg of II$^{GlcNAc}$. After incubation for 30 min at 37° C., the reaction was stopped by adding 1 ml ice-cold water. GlcNAc-6-Phosphate was separated from free Glc-NAc by anion-exchange chromatography on AG-1-X2 (50–100 mesh, Biorad). Activity is expressed as nmoles of sugar-P formed after 30 min. The HPr concentration was adjusted such that it was rate limiting in the overall phosphotransferase reaction. The inhibitory peptides were added to concentrations of 25 μm to 10 mM. Phosphorylation of GlcNAc in the absences of peptide was taken as 100%.

Pyruvate Formation Coupled to Lactate Dehydrogenase.

Pyruvate formed from phosphoenolpyruvate by enzyme I was converted to lactate in the presence of lactate dehydrogenase, and the concomitant consumption of NADH was followed spectrophotometrically at 340 nm. 1 ml of the reaction mixture contained 0.8 mM PEP, 0.2 mM NADH 30 pg lactate dehydrogenase, 50 mM KPi pH 7.5, 2.5 mM dithiothreitol, 2.5 mM NaF, 5 mm MgCl$_2$, and as substrate either 22.5 μM HPr or 50 to 150 μM of the peptide. The reaction was started by the addition of 0.75 μM enzyme 1. To measure the inhibition of enzyme I by the peptides, peptides were added at different concentrations. The inhibitory peptides are phosphorylated by enzyme I at a much slower rate than Hpr.

Growth Inhibition Assay.

An over night culture of E. coli K-12 UT580 grown in LB-medium was diluted 1:30 into soft agar (0.7% agarose in LB broth) at 40° C., and 3 ml of the diluted cell suspension were spread on LB agar plates. Filter discs (4.4 mm diameter) were placed in regular intervals on the solidified top agar. To each filter was added 10 μl of one of the different peptide stock solutions (20 μM to 80 μM). The agar plates were incubated over night at 37° C. The area of the clear zone around each filter disc was determined. The clear area is taken as a measure for the growth inhibitory activity of the peptide. Compare FIG. 4 and Table I on the following two pages.

TABLE I

Biological activities of peptides identified by phage display

| ID | peptide sequence | inhibition IC$_{50}$ (μM) | uncoupling P$_1$/peptide (× IC$_{50}$/h)[c] | growth inhibition (area/μM) |
|----|------------------|---------------------------|--------------------------------------------|-----------------------------|
| 1  | GLRFGKTRVHYLVLG  | 25   | 3.2   | 3.65 |
| 2  | SGRKSTRVHHWLLVL  | 60   | 6.6   | 3.05 |
| 3  | KMSRHRKPGA       | 100  | 22.2  |      |
| 4  | SSLRGHRWVY       | 120  | 50.3  |      |
| 5  | KISRHGKRGK       | 140  | 1.9   |      |
| 6  | KISRHGRPTG       | 1065 | 479.3 |      |
| 7  | RIHFIPRRGR       | 280  | 39.6  | 0.77 |
| 8  | RLHYLF[a]        | 375  | 64.2  | 0.90 |
| 9  | DGARLHYLF[a]     | 1200 | 132.3 |      |
| 10 | AcDGARLHYLF[a]   | 7600 | 15.2  |      |
| 11 | RHWSIF           | 400  |       | 1.30 |
| 12 | RHRTLF           | 410  |       |      |
| 13 | RHYLLF           | 500  |       | 0.83 |
| 14 | RHITSL           | 650  |       |      |
| 15 | RHITLF           | 1380 |       | 0.27 |
| 16 | MSRHRN           | 760  | 143.8 |      |
| 17 | PNGLHTRPA[b]     | 2600 |       |      |

TABLE I-continued

Biological activities of peptides identified by phage display

| ID | peptide sequence | inhibition IC$_{50}$ (μM) | uncoupling P$_i$/peptide (× IC$_{50}$/h)[c] | growth inhibition (area/μM) |
|---|---|---|---|---|
| 18 | MRLLKTLCFGLCG | 3500 | | |
| 19 | AcMRLLKTLCFVGLCG | >10,000 | | |

[a] Peptides Nr. 9 and 10 have at their amino terminus three extra residues (DGA) that are encoded by the coat protein pIII of M13. Ac; acetyl-.
[b] The amino acid sequence of peptide Nr 17 is identical with the sequence of the active site loop of HPr. Since this sequence was not found among the phage displayed peptides it was chemically synthesized and used for comparison.
[c] The rate of uncoupling is very low. It is calculated as μM NADH consumed per μM peptide per one hour multiplied by the IC$_{50}$. (μM). This modification allows to compare the approximate rates of phosphohydrolysis in spite of the widely different affinities (IC$_{50}$) of the peptides for enzyme.

TABLE 2

Biological activities of peptides identified from support-based combinatorial libraries.

| ID | peptide sequence | inhibition IC$_{50}$ (μM) | uncoupling P$_i$/peptide/h | growth inhibition MIC (μM) |
|---|---|---|---|---|
| 20 | KKFHLRK | 150 | 0.49 | 125.8 |
| 21 | KKFALRK[a] | none | | |
| 22 | KKFDLRK[b] | 820 | 0.05 | |
| 23 | XXKKWHLRKRXX | 150 | 0.43 | 44.7 |
| 24 | KKWHLRKR[c] | 30 | 0.3 | 63.0 |
| 25 | KGWHKRKK | 530 | 0.23 | |
| 26 | KKWHRRKK | 300 | 0.29 | |
| 27 | KKWHKRKK | 440 | 0.215 | |
| 28 | KKFHIRKR | 160 | 0.31 | |
| 29 | PNGLHTRPA[d] | 2600 | 0.07 | |
| 30 | Bio-PNGLHTRPA[e] | 4300 | — | |
| 31 | WHKR | 4900 | — | |
| 32 | Ac-WHKR[f] | 5800 | — | |
| | HPr protein | | 2.70 | |
| | tetracycline | | | 2.5 |

[a] peptide with no phosporylatable amino acid residue, derived from peptide 1.
[b] peptide with aspartate in place of histidine, derived from peptide 1.
[c] octapeptide derived from dodecapeptide 4.
[d] peptide with the sequence of HPr active site loop.
[e] biotinylated peptide to standardize in vitro enzymatic assays in micro titer plates.
[f] Ac: acetylated peptide.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

All publications and patent applications mentioned in the specifications are herein incorporated by reference to the same extent as if each individual publication or patent application was specifically and individually indicated to be incorporated by reference.

REFERENCES

Ammer, J., Brennenstuhl, M., Schindler, P., Höltje, J. V., and Zahler, H. (1979) Phosphorylation of streptozotocin during uptake via the phosphoenolpyruvate:sugar phosphotransferase system in *Escherichia coli*. Antimicrob. Agents Chemother. 16, 801–807.

Amster-Choder, O. and Wright, A. (1993) Transcriptional Regulation of the bgl Operon of *Escherichia-Coli* Involves Phosphotransferase System-Mediated Phosphorylation of a Transcriptional Antiterminator. J. Cell. Bioch. 51, 83–90.

Buhr, A., Daniels, G. A., and Emi, B. (1992) The glucose transporter of *Escherichia coli*. Mutants with impaired translocation activity that retain phosphorylation activity. J. Biol. Chem. 267, 3847–3851.

Christian, R. B., Zuckermann, R. N., Kerr J. M., Wang, L., and Malcolm, B. A. (1992) Simplified methods for construction, assessment and rapid screening of peptide libraries in bacteriophages. J. Mol. Biol. 227, 711–718.

Curtiss, R. and Kelly, S. M. (1987) *Salmonella typhimurium* deletion mutants lacking adenylate cyclase and cyclic AMP receptor protein are avirulent and immunognic. Infect. Immun. 55 30355–3043.

Curtiss, R., Goldschniidt, R. M., Fletchall, N. B., and Kelly, S. M. (1988) Avirulent *Salmonella typhimurium* delta cya delta crp oral vaccine strains expressing a streptococcal colonization and virulence antigen. Vacine 6, 155–160.

Eberstadt, M., Golic Grdadolnik, S., Gemmecker, G. Kessler, H., Buhr, A. and Erni, B. (1996) Solution structure of the IIB domain of the glucose transporter of *Escherichia coli*. Biochemistry, in press.

Eberstadt, M., Gemmecker, G., Golic Grdadolnik, S., Kessler, H., Buhr, A., Lanz, R. and Erni, B. (1996) The glucose transporter of *Escherichia coli:* NMR characterization of the phosphocysteine form of the IIB$^{Glc}$ domain and its binding interface with the IIA$^{Glc}$ subunit. submitted.

Erni, B. (1992) Grouptranslocation of glucose and other carbohydrates by the bacterial phosphotransferase system. Int. Rev. Cytol. 137A, 127–148.

Erni, B., Trachsel, H., Postma, P. W., and Rosenbusch, J. P. (1982) Bacterial phosphotransferase system. Solubilization and purification of the glucose-specific enzyme II from membranes of *Salmonella typhimurium*. J. Biol. Chem. 257, 13726–13730.

Felici, F., Luzzago, A., Folgori, A., and Cortese, R. (1993) Mimicking of discontinuous epitopes by phage-displayed peptides, II. Selection of clones recognized by a protective monoclonal antibody against the Bordetella pertussis toxin from phage peptide libraries. Gene 128, 21–27.

Hurley, J. H., Faber, H. R., Worthylake, D., Meadow, N. D., Roseman, S., Pettigrew, D. W., and Remington, S. J. (1993) Structure of the Regulatory Complex of *Escherichia coli* III$^{Glc}$ with Glycerol Kinase. Science 259, 673–677.

Jia, Z. C., Quail, J. W., Waygood, E. B., and Delbaere, L. T. J. (1993a) The 2.0-angstrom Resolution Structure of *Escherichia coli* Histidine-Containing Phosphocarrier Protein HPr—A Redetermination. J. Biol. Chem. 268, 22490–22501.

Jia, Z. C., Vandonselaar, M., Quail, J. W., and Delbaere, L. T. J. (1993b) Active-Centre Torsion-Angle Strain Revealed in 1.6 Angstrom-Resolution Structure of Histidine-Containing Phosphocarrier Protein. Nature 361, 94–97.

Kalbitzer, H. R. and Hengstenberg, W. (1993) The Solution Structure of the Histidine-Containing Protein (Hpr) from *Staphylococcus-aureus* as Determined by 2-Dimensional H-1-NMR Spectroscopy. Eur. J. Biochem. 216, 205–214.

Kelly, S. M., Bosecker, B. A. Curtiss, R. (1992) Characterization of protective properties of attenuated mutants of *Salmonella choleraesuis*. Infect. Immun. 60, 4881–4890.

Lengeler, J. W., Jahreis, K. and Wehmeier, U. F. (1994) Enzymes II of the phosphoenolpyruvate-dependent phosphotransferase systems: their structure and function in carbohydrate transport. Biochem. Biophys. Acta 1188, 1–28.

Liao, D. I., Silverton, E., Seok, Y. J., Lee B. R., Peterkofsky, A., Davies. D. R. (1996) The first step in sugar transport: crystal structure of the amino terminal domain of enzyme I of the *E. coli* PEP.sugar phosphotransferase system and a model of the phosphotransfer complex with HPr. Structure, 4, 861–872.

LiCalsi, C., Crocenzi, T. S., Freire, E. and Roseman, S. (1991) Sugar transport by the bacterial phosphotransferase system. Structural and thermodynamic domains of Enzyme I of *Salmonella typhimurium*. J. Biol. Chem. 266, 19519–19527.

Lux, R., Jahreis, K., Bettenbrook, K., Parkinson, J. S. and Lengeler, J. W. (1995) A communication link between the PTS carbohydrate uptake system and the chemotaxis signaling pathway of *Escherichia coli*. Proc. Natl. Acad. Sci. USA 92, 11583–11587.

Mao, Q., Schunk, T., Flükiger, K., and Erni, B. (1995) Functional reconstitution of the purified mannose phosphotransferase system of *Escherichia coli* into phospholipid vesicles. J. Biol. Chem. 270, 5258–5265.

Martin-Verstraete, I., Debarbouillé, M., Klier, A., and Rapoport, G. (1994) Interactions of wild-type and truncated LevR of *Bacillus subtilis* with the upstream activating sequence of the levanase operon. J. Mol. Biol. 241, 178–192.

Mayahara, H., Hirano, H., Saitoh, T., and Ogawa, K. (1967) The new lead citrate method for the ultrachemical demonstration of activity of non-specific alkaline phosphatase. Histochemie 11, 88.

Meins, M., Jenö, P., Maller, D., Richter, W. J., Rosenbusch, J. P., and Erni, B. (1993) Cysteine phosphorylation of the glucose transporter of *Escherichia coli*. J. Biol. Chem. 268, 11604–11609.

Meadow, N. D., Fox, D. K. and Roseman, S. (1990) The bacterial phosphoenolpyruvate:glycose phosphotransferase system. Annu. Rev. Biochem. 59, 497–542.

Mukhija, S. and Erni, B. (I 996) Purification by Ni$^{2+}$ affinity chromatography, and functional reconstitution of the transporter for N-acetylglucosamine of *Escherichia coli*. J. Biol. Chem. 271, 14819–14824.

Nishikawa, Y., Scotland, S. M., Smith, H. R. Willshaw, G. A. and Rowe, B. (1995) Catabolite repression of the adhesion of Vero cytotoxin-producing Escherichia coli serogroups 01557 an 0111. Mcrob. Pathog. 18, 223–229.

Postma, P. W., Lengeler, J. W. and Jacobson, G. R. (1993) Phosphoenolpyruvate: Carbohydrate phosphotransferase systems in bacteria. Microbiol. Rev. 57, 543–594.

Powell, B. S., Court, D. L., Inada, T., Nakamura, Y., Michotey, V., Cui, X., Reizer, A., Saier, M. H., and Reizer, J. (1995) Novel proteins of the phosphotransferase system encoded within the rpoN operon of *Escherichia coli*. Enzyme IIA$^{Ntr}$ affects growth on organic nitrogen and the conditional lethality of the era$^{ts}$ mutant. J. Biol. Chem. 270, 4822–4839.

Rajagopal, P., Waygood, E. B., and Klevit, R. E. (1994) Structural consequences of histidine phosphorylation:

NMR characterization of the phosphohistidine form of histidine-containing protein from *Bacillus subtilis* and *Escherichia coli*. Biochemistry 33, 15271–15282.

Roossien, F. F., Brink, J., and Robillard, G. T. (1983) A simple method for the synthesis of [$^{32}$P] phosphophoenolpyruvate via the pyruvate kinase exchange reaction at equilibrium. Biochim. Biophys. Acta. 760, 185–187.

Reizer, J., Hoischen, C., Reizer, A., Pham, T. N., and Saier, M. H. (1993) Sequence Analyses and Evolutionary Relationships Among the Energy-Coupling Proteins Enzyme-I and HPr of the Bacterial Phosphoenolpyruvate-Sugar Phosphotransferase System. Protein Sci. 2, 506–521.

Saier, M. H. (1993). Regulatory Interactions Involving the Proteins of the Phosphotransferase System in Enteric Bacteria. Journal of Cellular Biochemistry 51, 62–68.

Saier, M. H. and Reizer, J. (1994) The bacterial phosphotransferase system: New frontiers 30 years later. Molecular Microbiology 13, 755–764.

Saier, M. H., Chavaux, S., Deutscher, J., Reizer, J., and Ye, J. J. (1995) Protein phosphorylation and regulation of carbon metabolism in Gram-negative versus Gram-positive bacteria. TIBS 20, 267–271.

Scott, J. K., and Smith, G. P. (1990) Searching for peptide ligands with an epitope library. Science 249, 386–390.

Seok, Y. J., Lee, B. R., Zhu, P. P. and Peterkofsky, A. (1996) Importance of the carboxyl-terminal domain of enzyme I of the *Escherichia coli* phosphoenolpyruvate: Sugar phosphotransferase system for phosphoryl donor specificity. Proc. Natl Acad Sci. USA 93, 347–351.

Titgemeyer, F., Mason, R. E. and Saier, M. H. (1994) Regulation of the raffinose permease of *Escherichia coli* by the glucose-specific enzyme IIA of the phosphoenolpyruvate:sugar phosphotransferase system. J. Bacteriol. 176, 543–546.

van Nuland, N. A. J., Boelens, R., Scheek, R. M., and Robillard, G. T. (1995) High-resolution structure of the phosphorylated form of the histidine-containing phosphocarrier protein HPr from *Escherichia coli* determined by restrained molecular dynamics from NMR-NOE data. J. Mol. Biol. 246,180–193.

van Nuland, N. A. J., Grotzinger, J., Dijkstra, K., Scheek, R. M., and Robillard, G. T. (1992) Determination of the 3-Dimensional Solution Structure of the Histidine-Containing Phosphocarrier Protein HPr from *Escherichia coli* Using Multidimensional NNM Spectroscopy. Eur. J. Bioch. 210, 881–891.

van Nuland, N. A. J., Hangyi, I. W., van Schaik, R. C., Berendsen, H. J. C., van Gunsteren, W. F., Scheek, R. M., and Robillard, G. T. (1994) The High-Resolution Structure of the Histidine-Containing Phosphocarrier Protein Hpr from *Escherichia coli* Determined by Restrained Molecular Dynamics from Nuclear Magnetic Resonance Nuclear Overhauser Effect Data. J. Mol. BiolPhosphorylation of a Transcriptional Antiterminator. J. Cell. Bioch. 51, 83–90.

Weber, L., Wallbaum, S., Broger, C., and Gubernator, K. (1995) Optimierung der biologischen Aktivität von kombinatorischen Verbindungsbibliotheken durch einen genetischen Algorithmus. Angew. Chem. 107, 2452–2454.

Wittekind, M., Rajagopal, P., Branchini, B. R., Reizer, J., Saier, M. H. Jr. & Klevit, R. E. (1992) Solution structure of the phosphocarrier protein HPr from *Bacillus subtilis* by two-dimensional NMR spectroscopy, Protein Sci. 1, 1363–1376.

Yamamoto, K (1988) Alkaline phosphatase in Electron microscopic cytochemistry and immunochemistry in biomedicine (Ogawa, K., and Barka, T. eds.) CRC Press, Boca Raton.

---

What is claimed is:

1. A screening assay for the identification of specific peptide which acts as an antimicrobial by inhibiting or uncoupling enzyme I, said assay comprising:
   a) adding a test peptide to a reaction mixture containing enzyme I and phosphoenolpyruvate; and
   b) measuring pyruvate levels in the presence of lactate dehydrogenase and NADH, where increased levels of pyruvate serve as an indication that the test peptide has uncoupling or inhibitory activity of enzyme I of the bacterial phosphotransferase system.

2. A screening assay for the identification of specific peptide which acts as an antimicrobial by inhibiting or uncoupling enzyme I, said assay, comprising:
   a) adding a test compound to a reaction mixture containing enzyme I and phosphoenolpyruvate and a radiolabeled glucose or N-acetylglucoseamine phosphate acceptor; and
   b) isolating the radiolabeled phosphate acceptor and measuring the level of phosphorylation of the phosphate acceptor, where decreased levels of phosphorylation serve as an indication that the test compound has uncoupling of or inhibitory activity on enzyme I of the bacterial phosphotransferase system.

3. The assay of claim 2 where the radiolabeled phosphate acceptor is N-acetyl glucosamine.

4. The assay of claim 2 where the radiolabeled phosphate acceptor is glucose.

5. The assay of claim 1 or 2 wherein the peptides are synthesized from a combinatorial peptide library.

6. The assay of claim 1 or 2 wherein the peptides are expressed from a phage display library.

7. The assay of claim 1 or 2 wherein the peptide to be assayed contains either a histidine or cysteine residue.

8. The assay of claim 1 or 2 wherein the peptide to be assayed can be phosphorylated by enzyme I.

* * * * *

UNITED STATES PATENT AND TRADEMARK OFFICE
CERTIFICATE OF CORRECTION

PATENT NO.    : 6,245,502 B1
DATED         : June 12, 2001
INVENTOR(S)   : Bernhard Erni It is certified that error appears in the above-identified patent and that said Letters Patent is hereby corrected as shown below:

<u>Title page,</u>
Item [76], "Bernhard Emi" should be -- Bernhard ERNI --;
Item [73], insert -- Assignee:    ARPIDA, Dammstrasse 36, CH- 4142 Muenchenstein, Switzerland --;
Item [74], insert --*Attorney, Agent, or Firm* -- Pennie & Edmonds LLP --.

Signed and Sealed this

Twenty-second Day of October, 2002

Attest:

JAMES E. ROGAN
Attesting Officer           *Director of the United States Patent and Trademark Office*

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:1:

Lys Lys Phe His Leu Arg Lys
1             5

(2) INFORMATION FOR SEQ ID NO:2:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:2:

Lys Lys Phe Ala Leu Arg Lys
1               5

(2) INFORMATION FOR SEQ ID NO:3:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:3:

Lys Lys Phe Asp Leu Arg Lys
1               5

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: peptide
        (B) LOCATION: 1
        (D) OTHER INFORMATION: /label=Xaa /note= "wherein Xaa can be
            any amino acid (ix) FEATURE:
        (A) NAME/KEY: peptide
        (B) LOCATION: 2
        (D) OTHER INFORMATION: /label=Xaa /note= "wherein Xaa can be
            any amino acid (ix) FEATURE:
        (A) NAME/KEY: peptide
        (B) LOCATION: 11
        (D) OTHER INFORMATION: /label=Xaa
            /note= "wherein Xaa can be any amino acid"

(ix) FEATURE:
        (A) NAME/KEY: peptide
        (B) LOCATION: 12
        (D) OTHER INFORMATION: /label=Xaa /note= "wherein Xaa can be
            any amino acid"

(xi) SEQUENCE DESCRIPTION: SEQ ID NO:4:

Xaa Xaa Lys Lys Trp His Leu Arg Lys Arg Xaa Xaa
1               5                   10

(2) INFORMATION FOR SEQ ID NO:5:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:5:

Lys Lys Trp His Leu Arg Lys Arg
1               5

(2) INFORMATION FOR SEQ ID NO:6:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:6:

```
Lys Gly Trp His Lys Arg Lys Lys
 1               5
```

(2) INFORMATION FOR SEQ ID NO:7:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:7:

```
Lys Lys Trp His Arg Arg Lys Lys
 1               5
```

(2) INFORMATION FOR SEQ ID NO:8:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:8:

```
Lys Lys Trp His Lys Arg Lys Lys
 1               5
```

(2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:9:

```
Lys Lys Phe His Ile Arg Lys Arg
 1               5
```

(2) INFORMATION FOR SEQ ID NO:10:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:10:

```
Pro Asn Gly Leu His Thr Arg Pro Ala
 1               5
```

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: peptide
        (B) LOCATION: 1
        (D) OTHER INFORMATION: /label=Pro /note= "wherein a biotin
            molecule is covalently linked to Pro at position 1"

(xi) SEQUENCE DESCRIPTION: SEQ ID NO:11:

Pro Asn Gly Leu His Thr Arg Pro Ala
1               5

(2) INFORMATION FOR SEQ ID NO:12:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:12:

Trp His Lys Arg
1

(2) INFORMATION FOR SEQ ID NO:13:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: peptide
        (B) LOCATION: 1
        (D) OTHER INFORMATION: /label=Trp /note= "wherein Trp is
            acetylated"

(xi) SEQUENCE DESCRIPTION: SEQ ID NO:13:

Trp His Lys Arg
1

(2) INFORMATION FOR SEQ ID NO:14:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:14:

Gly Leu Arg Phe Gly Lys Thr Arg Val His Tyr Leu Val Leu Gly
1               5                   10                  15

(2) INFORMATION FOR SEQ ID NO:15:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
            (A) NAME/KEY: peptide
            (B) LOCATION: 11
            (D) OTHER INFORMATION: /label=Trp /note= "wherein Trp is
                acetylated"

(xi) SEQUENCE DESCRIPTION: SEQ ID NO:15:

Ser Gly Arg Lys Ser Thr Arg Val His His Trp Leu Leu Val Leu
1               5                   10                  15

(2) INFORMATION FOR SEQ ID NO:16:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:16:

Lys Met Ser Arg His Arg Lys Pro Gly Ala
1               5                   10

(2) INFORMATION FOR SEQ ID NO:17:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:17:

Ser Ser Leu Arg Gly His Arg Trp Val Tyr
1               5                   10

(2) INFORMATION FOR SEQ ID NO:18:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:18:

Lys Ile Ser Arg His Gly Lys Arg Gly Lys
1               5                   10

(2) INFORMATION FOR SEQ ID NO:19:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:19:

Lys Ile Ser Arg His Gly Arg Pro Thr Gly
1               5                   10

(2) INFORMATION FOR SEQ ID NO:20:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:20:

```
Arg Ile His Phe Ile Pro Arg Arg Gly Arg
 1               5                  10
```

(2) INFORMATION FOR SEQ ID NO:21:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:21:

```
Arg Leu His Tyr Leu Phe
 1               5
```

(2) INFORMATION FOR SEQ ID NO:22:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:22:

```
Asp Gly Ala Arg Leu His Tyr Leu Phe
 1               5
```

(2) INFORMATION FOR SEQ ID NO:23:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: peptide
        (B) LOCATION: 1
        (D) OTHER INFORMATION: /label=Xaa /note= "wherein Asp is
            acetylated"

(xi) SEQUENCE DESCRIPTION: SEQ ID NO:23:

```
Asp Gly Ala Arg Leu His Tyr Leu Phe
 1               5
```

(2) INFORMATION FOR SEQ ID NO:24:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:24:

```
Arg His Trp Ser Ile Phe
 1               5
```

(2) INFORMATION FOR SEQ ID NO:25:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:25:

Arg His Arg Thr Leu Phe
1           5

(2) INFORMATION FOR SEQ ID NO:26:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:26:

Arg His Tyr Leu Leu Phe
1           5

(2) INFORMATION FOR SEQ ID NO:27:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:27:

Arg His Ile Thr Ser Leu
1           5

(2) INFORMATION FOR SEQ ID NO:28:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:28:

Arg His Ile Thr Leu Phe
1           5

(2) INFORMATION FOR SEQ ID NO:29:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:29:

Met Ser Arg His Arg Asn
1           5

```
(2) INFORMATION FOR SEQ ID NO:30:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:30:

Pro Asn Gly Leu His Thr Arg Pro Ala
1               5

(2) INFORMATION FOR SEQ ID NO:31:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:31:

Met Arg Leu Leu Lys Thr Leu Cys Phe Gly Leu Cys Gly
1               5                   10

(2) INFORMATION FOR SEQ ID NO:32:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: peptide
        (B) LOCATION: 1
        (D) OTHER INFORMATION: /label=Met /note= "wherein Met is
            acetylated"

(xi) SEQUENCE DESCRIPTION: SEQ ID NO:32:

Met Arg Leu Leu Lys Thr Leu Cys Phe Val Gly Leu Cys Gly
1               5                   10
```